United States Patent [19]

Yogosawa

[11] 4,299,570
[45] Nov. 10, 1981

[54] OCCLUDATOR

[75] Inventor: Fumio Yogosawa, Tokyo, Japan

[73] Assignee: Sankin Kogyo Kabushiki Kaisha, Osaka, Japan

[21] Appl. No.: 138,365

[22] Filed: Apr. 8, 1980

[30] Foreign Application Priority Data

May 11, 1979 [JP] Japan .................................. 54-57839

[51] Int. Cl.³ ............................................. A61C 11/00
[52] U.S. Cl. ....................................... 433/62; 433/64; 433/65; 433/60
[58] Field of Search ....................... 433/62, 57, 60, 61, 433/63, 64, 65, 66, 67

[56] References Cited

U.S. PATENT DOCUMENTS

| D. 191,110 | 8/1961 | Weissman | 433/54 |
|---|---|---|---|
| 321,457 | 7/1885 | Smith | 433/65 |
| 431,849 | 7/1890 | Moffitt | 433/65 |
| 537,812 | 4/1895 | Bragg | 433/64 |
| 750,203 | 1/1904 | Knight | 433/64 |
| 824,096 | 6/1906 | Crate | 433/65 |
| 1,722,306 | 7/1929 | Murray | 433/63 |
| 1,814,750 | 7/1931 | Fritzenwallner | 433/64 |
| 4,096,632 | 6/1978 | Perry | 433/60 |

FOREIGN PATENT DOCUMENTS 1165823 10/1958 France .................................. 433/62

Primary Examiner—Gene Mancene
Assistant Examiner—John J. Wilson
Attorney, Agent, or Firm—Fleit & Jacobson

[57] ABSTRACT

An occludator for an artificial denture having an upper holder for holding an upper artificial denture and a lower holder for holding a lower artificial denture. The upper and lower holders are pivotable to facilitate an observation of occlusion and adjustable to obtain neutral occlusion.

3 Claims, 9 Drawing Figures

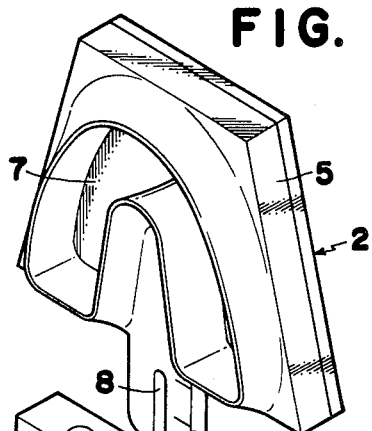
FIG. 4
FIG. 3
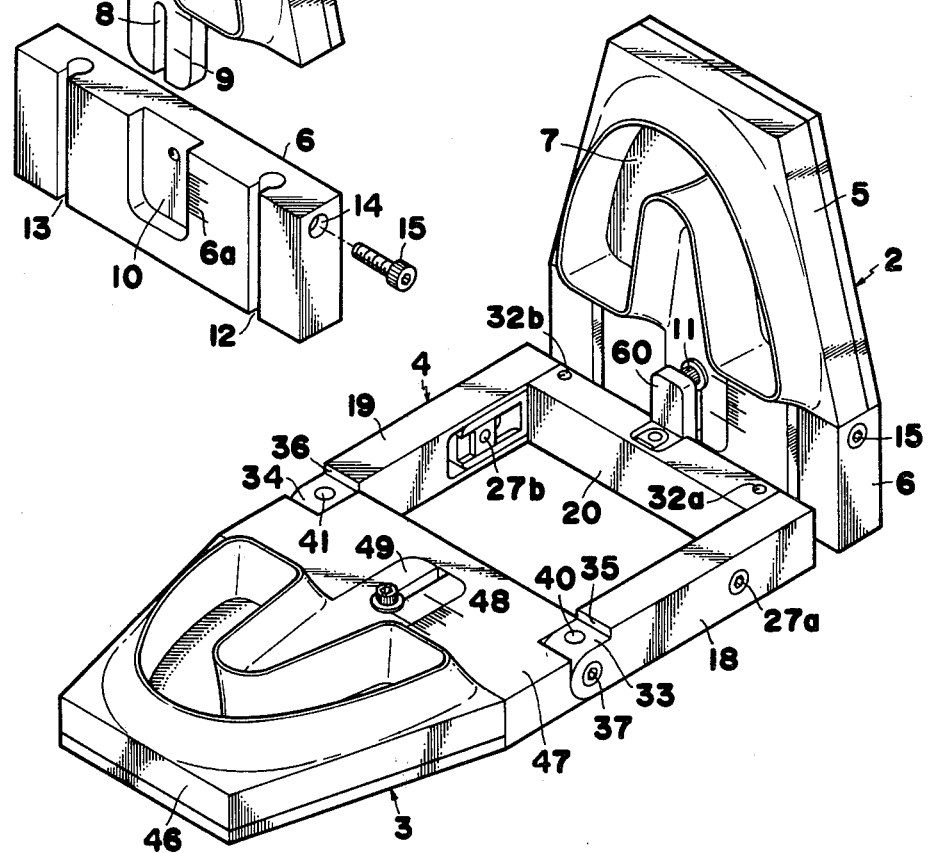
FIG. 9
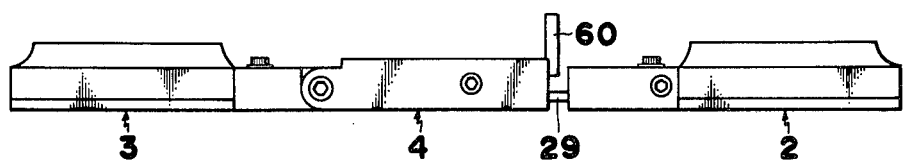

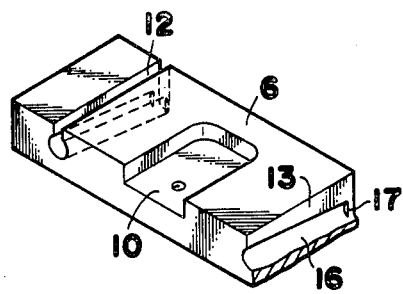
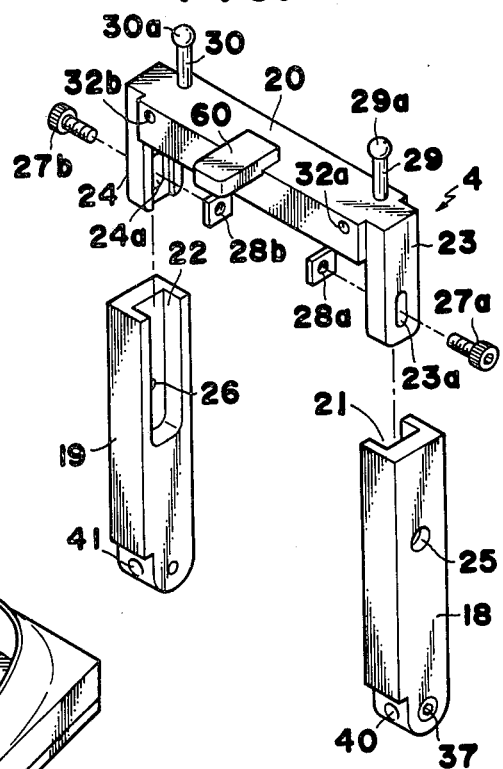
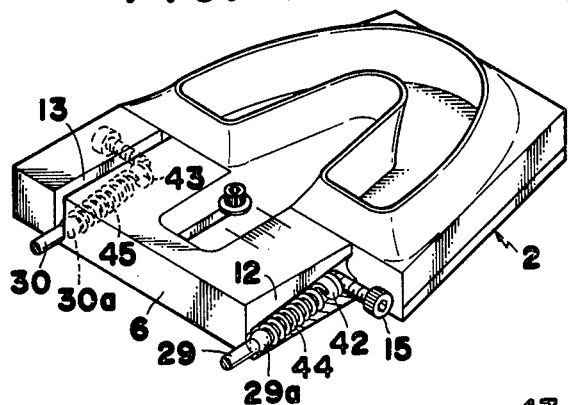
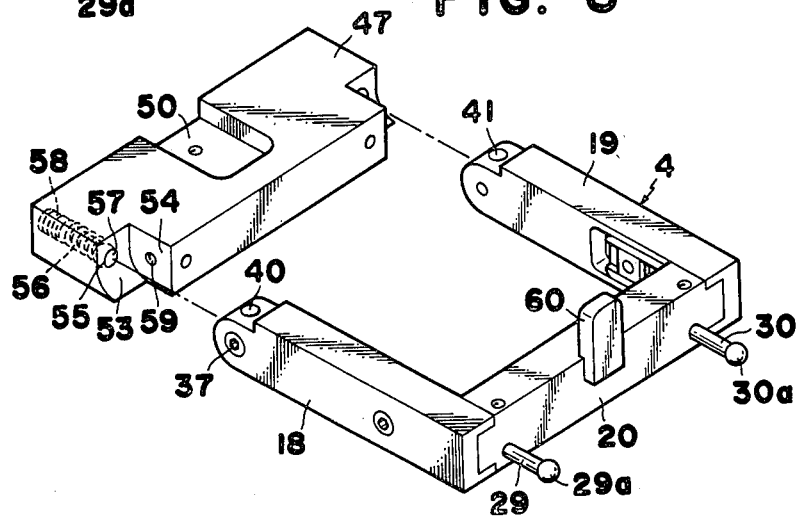

OCCLUDATOR

BACKGROUND OF THE INVENTION

The present invention relates to an occludator used with a full or partial artificial denture which permits a neutral occlusion.

The neutral occlusion means that upper and lower dental prostheses (i.e., false teeth) are in contact regularly with each other with balanced pressure when a user chews foods so that cutting and chewing of foods are established efficiently and pleasantly. In occlusal motion, it should be noted that a lower denture when worn by the user has not only a vertical movement but also complex movements, such as forward and backward movements. Accordingly, care should be taken so that the artificial denture meets with such complex movements.

Attempts have been made to provide such occludator as to establish neutral occlusion, but the conventional occludators presently used are complex in structure and design so as to meet with the aforesaid complex movement of the occlusal motion. Further, it is quite difficult in the conventional occludators to observe and examine the orthodontic operation of malposition or functional aberration.

SUMMARY OF THE INVENTION

Accordingly, an object of the present invention is to provide an improved occludator which permits a ready observation of the denture, and easy manipulation and operation.

Another object of the present invention is to provide an occludator which permits adjustment of upper and lower holders which hold upper and lower artificial dentures.

Another object of the present invention is to provide an occludator which can be operated readily without the involvement of substantial labor or difficulty.

Another object of the present invention is to provide an occludator which has a simple structure.

Briefly, an occludator in the present invention has a first holder for an upper denture, a second holder for a lower denture, and leg means for pivotally securing the holders. The holders are pivotally secured to ends of the leg means so that the holders are pivoted into positions at right angles relative to a plane of the leg means.

Other objects and features of the present invention will become apparent from the detailed description of the invention, which will be made with reference to the accompanying drawings.

BRIEF DESCRIPTION OF THE DRAWINGS

FIG. 3 is a perspective view of the occludator shown in FIG. 1, showing the lower holder pivotally opened whereas the upper holder remains in its relative position of FIG. 1.

FIG. 4 is an exploded perspective view of the upper holder.

FIG. 5 is a perspective view of a portion of the upper holder.

FIG. 6 is an exploded perspective view of elements of a leg device for pivotally holding the upper and lower holders.

FIG. 7 is a partly cut-out perspective view of the upper holder.

FIG. 8 is an exploded perspective view showing a connection between the lower holder and the leg device.

FIG. 9 is a side view of the occludator showing the upper and lower holders pivotally opened.

DETAILED DESCRIPTION OF THE INVENTION

Figure 1:
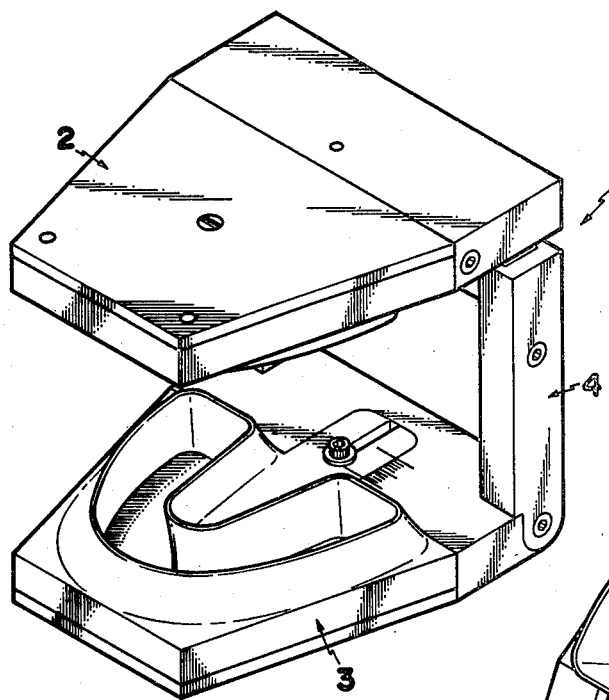
FIG. 1 is a perspective view of an occludator embodying the present invention, showing an upper holder in an opposed relation with a lower holder.

In FIG. 1, an occludator 1 according to the present invention has, in confronting relation, an upper holder 2 for securing an upper denture (not shown), a lower holder 3 for a lower denture (not shown) and supporting body 4 which pivotally holds the upper and lower holders in a confronting relation.

Figure 2:
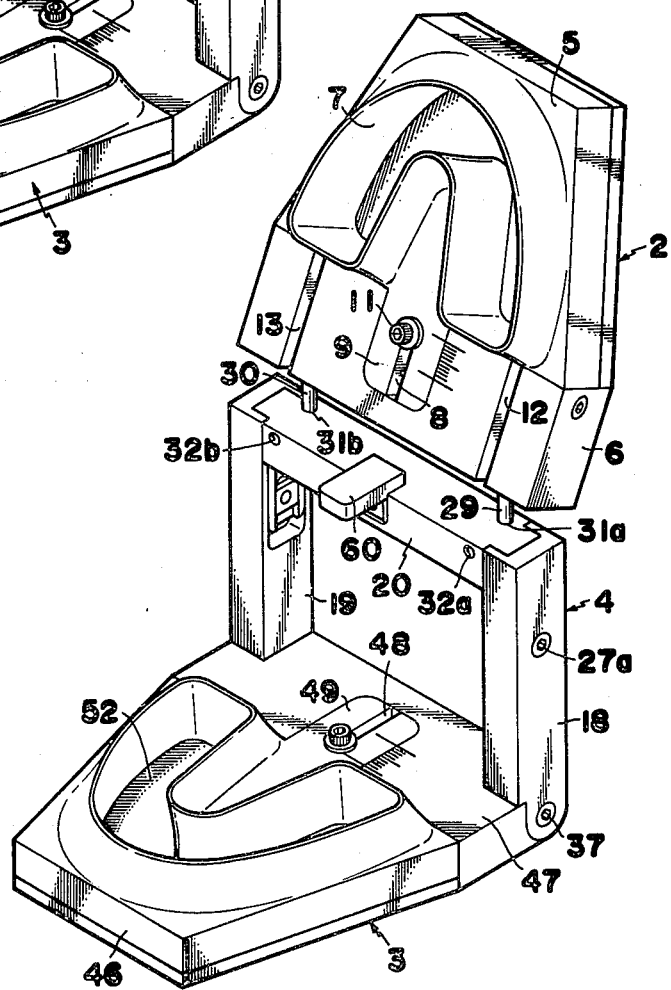
FIG. 2 is a perspective view of the occludator shown in FIG. 1, showing the upper holder pivotally opened.

Referring to FIGS. 2 and 3, the upper holder 2 has a denture holding plate 5 made of corrosion-free metals, such as aluminum alloy and a plastic base 6 detachably connected to the denture holding plate 5. The plate 5 has a groove 7 in the form of alphabetical "U" for securing therein the upper denture, and a projection 9 formed integral therewith. The projection 9 has an elongated portion 8, as illustrated in FIG. 4, which has a thicknes of about ½ of that of the denture holding plate 5. The base 6 which can be detachably connected with the denture holding plate 5 has a recess 10 for nesting therein the projection 9. The base 6 and the denture holding plate 5 are connected together by means of a bolt 11 after the projection 9 is suitably fitted into the recess 10. Reference numeral 6a designates a scale carved on the surfaces of the projection and of the base for adjustment of the position of the denture holding plate 5 relative to the base 6.

As illustrated in FIGS. 4 and 5, the base 6 has on its surface two grooves 12, 13 which are symmetrical relative to the recess 10, and threaded holes 14 at the sides for engagement with screws 15. The grooves 12, 13 have a concave portion 16 on the sides of each of the grooves as illustrated in FIG. 5. The concave portion 16 is formed along substantially all of the length of the grooves 12, 13, but ends with a shoulder 17 at one side of the base 6. In place of providing the concave portion 16, the grooves 12, 13 may be formed in a suitable form so that connecting rods 29, 30, which will be described later, may not be removed from the grooves.

Supporting legs 4 will be described with reference particularly to FIGS. 2, 3 and 6. The supporting body 4 has two legs 18, 19 which have grooves 21, 22 for detachably receiving a beam 20. The beam 20 has extensions 23, 24 formed integral at the ends thereof which will be inserted into the grooves 21, 22. The extensions 23, 24 have longitudinal slots 23a, 24a, respectively, and the legs 18, 19 have slots 25, 26, through which bolts 27a, 27b are inserted so that the legs 18, 19 are engaged with the extensions 23, 24 of the beam 20 by means of the bolts 27a, 27b and nuts 28a, 28b. The beam 20 has two metal rods 29, 30 which extend adversely relative to extensive direction of the legs 23, 24 and have balls 29a, 30a at the extended ends of the rods. The rods 29, 30 with balls 29a, 30a, respectively, are inserted into the aforementioned grooves 12, 13 and serve as a pivotal connection of the upper holder 2.

In the illustrated embodiment of the invention, the rods 29, 30 are inserted into holes 31a, 31b and are fixed by screws (not shown) in threaded holes 32a, 32b which are formed perpendicularly to the holes 31a, 31b for the rods.

The legs 18, 19 have offset portions 33, 34 and shoulders 35, 36 respectively, at the ends thereof. The ends of the legs 18, 19 are round shaped as illustrated in FIGS. 3 and 6 and are pivotally connected to the lower holder 3 by means of screws 37. On the offset portions are provided conical depressions 40, 41 which will be engaged with balls 57, which will be described later, positioned on the side of the lower holder 3 when the supporting body 4 is pivoted to the standing posture as illustrated in FIGS. 1 and 2. Reference numeral 60 is a stopper plate connected to a middle portion of the beam 20 for supporting the upper holder 2 at right angles to the supporting body 4.

Referring now to FIG. 7, within the elongated grooves 12, 13 formed on the base 6 of the upper holder 2 there are provided springs 44, 45 and disc members 42, 43 at one end of each of the springs. The other ends of each the springs are contacted with the aforementioned balls 29a, 30a disposed integral with the rods 29, 30. The disc members 42, 43 are supported by the screws 15 which extend transversely to the substantial lengthwise direction of the grooves 12, 13.

FIG. 8 shows a connection between the lower holder 3 and the supporting body 4. The lower holder 3 is constructed similar with the aforementioned upper holder 2 but does not have grooves similar to the grooves 12, 13 of the upper holder 2 and the associated elements therewith. It will be understood that the lower holder 3 is substantially identical to the upper holder 2 except for the elongated grooves and the associated elements for these grooves. The lower holder 3 has a denture holding plate 46 having a U shaped groove 52, and a base 47 which can be releasably connected with the denture holding plate 46. The denture holding plate 46 has a projection 49 which has a cut-out portion 48, and the base 47 has a recess 50 for securing therein the projection 49.

In FIG. 8, the two legs 18, 19 are pivotally connected to the lower holder 3 in quite a similar manner with each other, and one of them will be described for simplicity. The base 47 has cut-out portion at the edge to form a curved inclination 53 and a side 54. A slot 55 is provided at the central portion of the curved inclination 53, and a spring 56 together with a ball 57 at an end and a screw at the other are disposed within the slot 55 so that the ball 57 is pressed outwardly by the resilient force of the spring 56. The resilient force of the spring can be adjusted by means of the screw 58. The side 54 adjacent to the curved inclination 53 has a threaded hole 59 with which a screw (not shown) inserted through a hole 37 of the leg 18 is engaged so that the leg 18 is pivotally connected to the base 47 of the lower holder 3. The lower holder 3 is pivotable at right angles relative to the supporting body 4. When the lower holder is pivoted at right angles relative to the supporting body 4 as illustrated, for example, in FIGS. 1 and 2, the ball 57 is received in the conical depression 40 formed on the offset portion, with the result that the right-angled posture is maintained.

As described above, the occludator according to the present invention permits a pivotal movement of not only the upper holder 2 but also the lower holder 3 in such a manner that the both holders 2, 3 are positionable in the same plane as that of the supporting body, as illustrated in FIG. 9. Namely, the upper and lower holders are pivotally opened in a flat posture, and therefore high efficiency of the working and operation can be achieved. Besides, position of the denture holding plates 5 and 46 and distance between the upper and lower holders 2, 3 can be adjusted. Therefore, occlusion and occlusal surface of the artificial denture can be easily observed and neutral occlusion and operation therefor can be accomplished easily. Furthermore, since the upper holder 2 can be shifted in its lateral position relative to the lower holder 3 by the combination of rods 29, 30 and springs 44, 45, an easy observation of the occlusion can be accomplished, and the two leg structure of the supporting body 4 permits an observation of occlusal surface of the artificial denture from the rear position of the occludator.

Though the present invention has been described with reference to the preferred embodiment thereof, many alterations and modifications may be made within the spirit of the invention.

What is claimed is:

1. An occlusion device for use in examination of occlusion of artificial dentures comprising:
   a first holder having a substantially U-shaped groove for securing therein a first of two artificial dentures,
   a second holder having a substantially U-shaped groove for securing therein a second of the two artificial dentures,
   a supporting device having two parallel legs and a beam member, said beam member being connected at corresponding end portions of said legs,
   means for pivotally connecting said supporting device to said first holder, and
   means for pivotally connecting said supporting device to said second holder, said first holder having a denture holding plate and a base plate detachably connected to said denture holding plate, said denture holding plate having said U-shaped groove, said base plate having two parallel grooves on one surface thereof, said beam member of the supporting device having two rods projecting outwardly and having a substantially spherical member at a projected end of each of said rods, said spherical members being nested in predetermined positions within said parallel grooves such that said first holder is pivotally engaged with said rods, said second holder having a denture holding plate and a base detachably connected to said denture holding plate of the second holder.

2. The occlusion device according to claim 1, in which said beam member is adjustably engaged with said end portions of said legs.

3. The occlusion device according to claim 1 or 2, in which each of said legs has a round shaped end and an offset portion adjacent said round shaped end forming a shoulder, said offset portion having a depression, said base of said second holder having two cut-out edges for pivotally engaging said legs therewith, said cut-out edges each having a slightly curved slant portion and a spring-biased projection at said slant portion, whereby when said second holder is pivoted at right angles relative to said supporting device, said projection is fitted into said depression with said shoulder being in abutment against a plane of said base of the second holder, thereby maintaining a right angled position of said second holder relative to said supporting device.

* * * * *